(12) United States Patent
Hedlund et al.

(10) Patent No.: US 6,479,468 B1
(45) Date of Patent: Nov. 12, 2002

(54) MODIFIED POLYSACCHARIDES EXHIBITING ALTERED BIOLOGICAL RECOGNITION

(75) Inventors: Bo E. Hedlund, New Brighton, MN (US); Thomas P. Weber, San Diego, CA (US); Paul R. Dragsten, Chanhassen, MN (US); Gregory J. Hanson, Fridley, MN (US); Philip E. Hallaway, Minneapolis, MN (US)

(73) Assignee: Biomedical Frontiers, Inc., Minneapolis, MN (US)

( * ) Notice: Subject to any disclaimer, the term of this patent is extended or adjusted under 35 U.S.C. 154(b) by 0 days.

(21) Appl. No.: 09/555,994

(22) PCT Filed: Dec. 9, 1998

(86) PCT No.: PCT/US98/26132

§ 371 (c)(1),
(2), (4) Date: Aug. 1, 2000

(87) PCT Pub. No.: WO99/29328

PCT Pub. Date: Jun. 17, 1999

Related U.S. Application Data

(60) Provisional application No. 60/069,079, filed on Dec. 9, 1997, and provisional application No. 60/069,095, filed on Dec. 11, 1997.

(51) Int. Cl.[7] ............................ A61K 31/70; C08B 31/18
(52) U.S. Cl. ................................. 514/60; 536/105
(58) Field of Search .................. 514/54, 59, 60; 536/105

(56) References Cited

U.S. PATENT DOCUMENTS

| 4,419,365 A | 12/1983 | McLachlan |
| 4,863,964 A | 9/1989 | Hedlund et al. |
| 4,987,253 A | 1/1991 | Bergeron |
| 5,217,998 A | 6/1993 | Hedlund et al. |
| 5,268,165 A | 12/1993 | Hedlund et al. |
| 5,493,053 A | 2/1996 | Bergeron, Jr. |
| 5,847,110 A | 12/1998 | Dragsten et al. |

FOREIGN PATENT DOCUMENTS

| DE | 1186076 | 10/1961 |

OTHER PUBLICATIONS

Sloan, et al., "Properties Of Periodate Oxidized Starch", Industrial and Engineering Chemistry 48, 11651172 (1956).
Bobbit, J.M., "Periodate Oxidation Of Carbohydrates", Advances in Carbohydrate Chemistry 16, 1–41 (1961).

*Primary Examiner*—Elli Peselev
(74) *Attorney, Agent, or Firm*—Merchant & Gould P.C.

(57) ABSTRACT

The invention relates to polysaccharides, polysaccharide conjugates with altered biological properties, and methods to produce these polysaccharides and conjugates.

11 Claims, 4 Drawing Sheets

Figure 1: In-vitro Amylase Digestions of Several Modified Starch Products

Figure 2: Blood Clearance in Rats of Several Modified Starch Products

In-vitro Amylase Digestions of Several Modified Starch-DFO Products

Blood Clearance of Several Modified Starch-DFO Products**

MODIFIED POLYSACCHARIDES EXHIBITING ALTERED BIOLOGICAL RECOGNITION

This application claims the benefit of provisional applications 60/069,079 filed Dec. 9, 1997 and 60/069,095 filed Dec. 11, 1997.

BACKGROUND OF THE INVENTION

Unmodified polysaccharides can have undesirable biological properties, such as rapid clearance from circulation, rapid degradation, and/or allergenicity. Two polysaccharides that are commonly employed in pharmaceutical compositions and therapeutic methods include starch and dextran.

Starch is a naturally occurring, highly biocompatible polymer. When starch is introduced into the bloodstream it is rapidly digested by amylase. The fragments of the digested product are rapidly cleared from the vascular compartment through glomerular filtration and/or metabolism. For this reason hydroxyethyl starch (rather than starch) has been used as a long lasting plasma volume expander for several clinical indications. The hydroxyethylation of the starch molecule serves to slow the rate of digestion/excretion of the polymer.

Hydroxyethylation of starch using ethylene oxide or 2-chloroethanol has been common practice for production of colloidal plasma volume expanders. These processes have numerous disadvantages including employing highly toxic ethylene oxide, difficulty in controlling the extent of hydroxyethylation, inability to select among starch hydroxyl groups, toxic by products, and high cost. For example, hydroxyethylation with ethylene oxide occurs at any hydroxylic site, including sites that have already been hydroxyethylated, and with solvent, residual water, and impurities or side products in the reaction mixture. Lack of selectivity among sites on the starch molecule requires extensive hydroxyethylation of the starch, although modification of certain specific sites offers a greater degree of protection from enzymatic degradation.

Dextran has been used for a variety of pharmaceutical and therapeutic preparations over the past 40–50 years. The wide use of dextrans has included purified native dextrans for plasma replacement/volume expansion, dextran-active conjugates, iron-dextran iron supplements, and dextran coated particles for MRI contrast agents. For the most part dextran in a highly purified form is well tolerated by most of the patient population. However severe anaphylactoid responses are known to occur, and are in some cases severe enough to result in death.

These undesirable properties of polysaccharides employed in pharmaceutical compositions and therapeutic methods indicates the need for modified polysaccharides, such as modified starches and modified dextrans, that have more desirable biological properties than the native or unmodified polysaccharides.

SUMMARY OF THE INVENTION

The present invention relates to modified polysaccharides that have more desirable biological properties than the native or unmodified polysaccharides, pharmaceutical compositions including these modified polysaccharides, methods employing these modified polysaccharides, and methods of reducing the undesirable biological properties of these modified polysaccharides. Preferably, the modified polysaccharide is an oxidized and reduced polysaccharide. Preferably the polysaccharide is reduced with periodate. In a pharmaceutical composition the oxidized and reduced polysaccharide can be formulated in a pharmaceutically acceptable vehicle.

Preferred polysaccharides for modification according to the present invention include starch and/or dextran. An oxidized and reduced starch preferably exhibits a longer vascular half-life than unmodified starch, slower degradation by amylase than unmodified starch, and/or slower clearance from an animal than unmodified starch. An oxidized and reduced soluble dextran preferably exhibits reduced allergenicity compared to dextran. Preferably, the greater the extent of oxidation of the polysaccharide, the greater the vascular half-life, the slower the degradation, the slower the clearance, and/or the smaller the allergenicity.

The modified polysaccharide can be a component of or be employed to form a conjugate, such as a conjugate with a chelator. A preferred chelator is deferoxamine (DFO).

A method of the invention includes increasing the vascular half life of starch by oxidizing and reducing the starch, and administering the oxidized and reduced starch into the circulation of a mammal. In another embodiment, the method of the invention includes decreasing the allergenicity of dextran by oxidizing and reducing the dextran, and administering the oxidized and reduced dextran into the circulation of a mammal. The dextran or starch administered can include a conjugate of the dextran or starch.

DETAILED DESCRIPTION OF THE INVENTION

Figure 1:
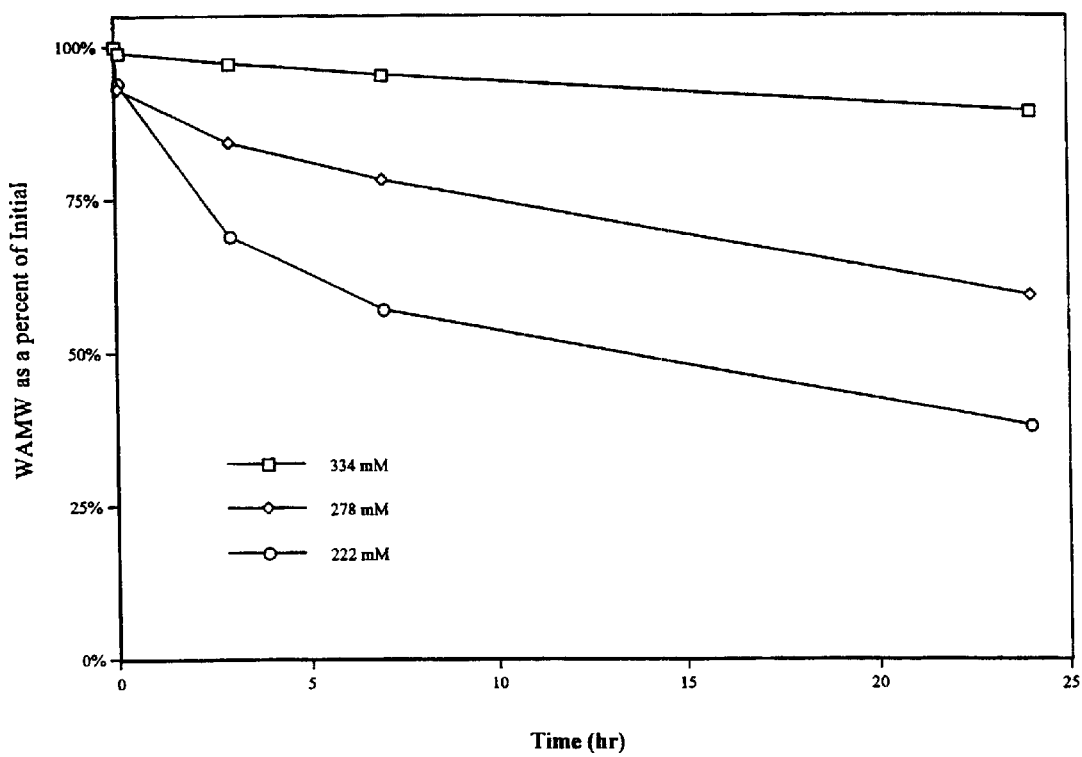
FIG. 1 illustrates a plot of the change in the Weight Average Molecular Weight (WAMW) as a function of time for modified starches upon treatment with amylase.

The present invention relates to modified polysaccharides that have more desirable biological properties than the native or unmodified polysaccharides, pharmaceutical compositions including these modified polysaccharides, methods employing these modified polysaccharides, and methods of reducing the undesirable biological properties of these modified polysaccharides.

Unmodified polysaccharides can have undesirable biological properties, such as rapid clearance from circulation, rapid degradation, and/or allergenicity. Unmodified starch, for example, is rapidly degraded and cleared from a mammal's circulation. Unmodified dextran is strongly, and perhaps fatally, allergenic in a proportion of mammals. Desirable properties for polysaccharides include slower clearance from the circulation, slower enzymatic digestion, and/or decreased allergenicity. Starch modified according to the present invention exhibits slower degradation by amylase and increased vascular half life. Dextran modified according to the present invention exhibits decreased and acceptable allergenicity.

Modified Polysaccharides

Polysaccharides suitable for use in the present invention include dextrans and hyaluronic acid, starch and starch derivatives, and the like. Polysaccharide starting materials such as dextrans and starches are commercially available as water-soluble preparations or as solutions. See *Remington's Pharmaceutical Sciences*, A. Osol., ed., Mack Publishing (16th ed. 1980) at pages 759–761. Polysaccharides of the invention include those described in U.S. Pat. Nos. 4,863,964, 5,217,998, and 5,268,165, the disclosures of which are incorporated herein by reference.

The present invention includes a polysaccharide that has been modified by oxidation followed by reduction, includes a pharmaceutical composition of the modified polysaccharide, includes a method for modifying a polysaccharide by oxidation and reduction, and includes a method of controlling biological properties of a polysaccharide through such modification. Oxidation followed by reduction can slow digestion, reduce allergenicity, and provide desirable alterations of other biological properties of the resulting biocompatible polysaccharide. The degree or extent to which hydroxyl groups on the polysaccharide are modified can be easily controlled, which provides a method to select the degree of modification of the biological property. For example, the reaction of periodate with polysaccharides is rapid and stoichiometric. The degree of oxidation of the polysaccharide molecule is homogeneous and easily and precisely controlled.

The resulting oxidized and reduced polysaccharide can be employed in methods and compositions that currently employ native polysaccharides or conventionally modified polysaccharides. Such methods and compositions include a colloidal plasma volume expander, hemodilution, a priming solution for a heart/lung bypass machine, an organ preservation solution, a cryoprotectant solution, and the like. Furthermore, the present method and modified polysaccharide provide control of the degree of oxidation of the polysaccharide, so that the modification of the polysaccharide can be selected to provide beneficial biological properties for each of these different uses. For example, as few as about 10% or as many as 100% of all, or of a class of, hydroxyl groups on a polysaccharide can be oxidized and reduced to alter its biological properties. Preferably the hydroxyl groups are vicinal hydroxyl groups, and oxidation is accomplished employing periodate. Preferably, about 30% to about 60% of all, or of a class of, hydroxyl groups on a polysaccharide can be oxidized and reduced to slow the rate at which the modified polysaccharide is degraded, digested, or cleared from an animal compared to the unmodified polysaccharide. Preferably, about 20% to about 80% of all, or of a class of, hydroxyl groups on a polysaccharide can be oxidized and reduced to reduce the allergenicity of the modified polysaccharide compared to the unmodified polysaccharide.

The polysaccharide to be modified can be a component of a polysaccharide-drug conjugate, or the modified polysaccharide can be employed to form a polysaccharide-drug conjugate. The effects of modification according to the invention on a polysaccharide-drug conjugate can be the same, e.g. slower degradation and/or reduced allergenicity, as modification of the polysaccharide itself. However, modification of a polysaccharide-drug conjugate or forming a polysaccharide-drug conjugate from a polysaccharide modified according to the invention can have additional beneficial effects as well.

For example, the vascular half life or plasma residence time of a polysaccharide-drug conjugate may be controlled by selection of appropriate degree of polysaccharide oxidation. When degradation of the polysaccharide or of a polysaccharide conjugate controls release of the drug, this invention provides a method for selecting controlled pharmacokinetics or sustained release of the drug. In this case, the degree of polysaccharide oxidation is selected for desired vascular half-life or release rate providing optimum effectiveness for each different polysaccharide-drug conjugate system and specific clinical indication.

Circumstances in which control of the rate of degradation of a polysaccharide conjugate can alter the effect of the conjugate or the drug released include: 1) The drug-polysaccharide conjugate is not pharmacologically active, but after cleavage of the backbone the fragments of the drug-polysaccharide conjugate become pharmacologically active. 2) The drug-polysaccharide conjugate is active, and upon cleavage the fragments (active or not) are more rapidly excreted. 3) Both the drug-polysaccharide conjugate and fragments are pharmacologically active but increased residence time, localization or compartmentalization of the polysaccharide-drug conjugate and fragments results from modification. 4) The pharmacological profile of the active conjugated to the polymer changes upon cleavage of the polysaccharide backbone. 5) Encapsulation of a drug within a polymeric shell of polysaccharide results in control of release of the drug from the capsule, and degradation of the shell is altered by modification of the polysaccharide. Other polysaccharides and polysaccharide conjugates that can benefit from modification according to the present invention include: conjugates in which the active component is a nutritional compound, a pharmaceutical, an enzyme, a contrast agent, an herbicide, an insecticide, or the like; polysaccharides employed in compositions in which control of the rate of degradation is desired, such as with biodegradable polymers, coatings, or timed release granules.

Modified Starch

The present invention includes starch that has been modified by oxidation followed by reduction, includes a pharmaceutical composition of the modified starch, includes a method for modifying starch by oxidation and reduction, and includes a method of controlling biological properties of starch through such modification. Oxidation followed by a reduction step slows digestion of the resulting biocompatible starch, and can also slow the rate of clearance from an animal. The degree or extent to which hydroxyl groups on the starch are modified can be easily controlled. Control and selection of the degree of oxidation determines the rate of enzymatic digestion (and resulting persistence or clearance-excretion) of the modified starch. Thus, the present invention provides a method to determine and select the vascular half life of a modified starch or of a conjugate of modified starch.

The reaction of periodate with starch is rapid (reaction goes to completion in a matter of minutes), specific for cleaving the bond between vicinal hydroxyl groups, and stoichiometric. Therefore the degree of oxidation of the starch molecule is homogeneous and easily controlled. Preferably the hydroxyl groups oxidized are vicinal hydroxyl groups, and oxidation is accomplished employing periodate.

It has been demonstrated that the oxidation/reduction of starch limits the rate at which it is digested by amylase. Higher degrees of oxidation of the starch molecule result in slower rates of digestion. Similarly, it has been demonstrated that oxidation/reduction of starch slows the rate at which it is cleared from an animal. Higher degrees of oxidation of the starch molecule result in slower rates of clearance. By selection of the appropriate degree of oxidation, a desired rate of digestion or clearance can be obtained. For example, as few as about 20% or as many as 90% of all, or of a class of, hydroxyl groups on a starch can be oxidized and reduced to alter biological properties, such as its rate of digestion or clearance from an animal. Preferably, about 30% to about 60%, of all, or of a class of, hydroxyl groups on a starch can be oxidized and reduced to slow the rate at which the modified starch is degraded, digested, or cleared from an animal compared to the unmodified starch. Under certain conditions, starch in which about 30% of all, or of a class of, hydroxyl groups on a starch are oxidized and reduced is digested by amylase at a rate nearly as fast as unmodified starch. Under these certain conditions, starch in which about 60% of all, or of a class of, hydroxyl groups on a starch are oxidized and reduced is only very slowly digested by amylase, and the starch can be nearly inert to such digestion.

The resulting oxidized and reduced starch can be employed in methods and compositions that currently employ conventional starches, such as hydroxyethyl starch. Such methods and compositions include a colloidal plasma volume expander, for hemodilution, a priming solution for a heart/lung bypass machine, a donor organ preservation solution, and the like. Furthermore, the present method and modified starch provide control of the degree of oxidation of the starch, so that the modification of the starch can be selected to provide the optimum vascular half life for each of these different uses. The starch to be modified can be a component of a starch-drug conjugate, or the modified starch can be employed to form a starch-drug conjugate. The effects of modification according to the invention on a starch-drug conjugate can be the same, e.g. slower degradation and/or reduced allergenicity, as modification of the polysaccharide itself. However, modification of a starch-drug conjugate or forming a starch-drug conjugate from a starch modified according to the invention can have additional beneficial effects as well.

For example, the rate of excretion (or release) of starch polymer (or starch polymer conjugate) can be controlled and selected for a particular use. Modified starch can be produced with vascular persistence selected, for example, for use as a conjugate in a medical contrast agent with a vascular half life of about 2 to about 4 hours; for metal poisoning therapy, which requires the drug to remain in the body for about 4 to about 24 hours; for plasma volume expansion, which requires a modified starch lasting about 12 to about 48 hours; or for iron overload, which requires the modified starch to stay in the circulation for about 2 to about 5 days. A starch that is more than about 30% oxidized and reduced, preferably about 30% to about 45% is suitable for the applications requiring a shorter half life. A starch that has approaching about 60% of its hydroxyl groups oxidized and reduced, preferably about 45% to about 60% is suitable for the applications requiring a longer half life.

The vascular half life or plasma residence time of a starch-drug conjugate may be controlled by selection of appropriate degree of starch oxidation. When degradation of the starch of a starch conjugate controls release of the drug, this invention provides a method for selecting controlled or sustained release of the drug. In this case, the degree of starch oxidation is selected for desired vascular half-life (or release rate) providing optimum effectiveness for each different starch-drug conjugate system and specific clinical indication.

Circumstances in which control of the rate of degradation of a starch conjugate can alter the effect of the conjugate or the drug released include: 1) The drug-starch conjugate is not pharmacologically active, but after cleavage of the backbone the fragments of the drug-starch conjugate become pharmacologically active. 2) The drug-starch conjugate is active, and upon cleavage the fragments (active or not) are rapidly excreted. 3) Both the drug-starch conjugate and fragments are pharmacologically active but increased residence time and localization or compartmentalization of the starch-drug conjugate and fragments results from modification. 4) The pharmacological profile of the active conjugated to the polymer changes upon cleavage of the starch backbone. 5) Encapsulation of drug within a polymeric shell of starch results in control of release of drug from the capsule, and degradation of the shell is altered by modification of the starch.

Modified Dextran

Chemical modification of dextran can reduce, minimize, or eliminate an allergenic reaction to native dextran, to dextran derived conjugates, or to dextran containing formulations, which are experienced in some humans (and other warm blooded species). The anaphylactic response can be severe enough to cause death, as noted in the Physicians Desk Reference product information for "INFeD" (Page 2478, Edition 51, 1997).

Dextran has been used for many years for various medical therapies and compositions, including plasma volume expansion, and hemodilution. Dextran is often preferred to other colloids used for plasma volume expansion due in part to the ability of the manufacturer to control properties such as viscosity, average molecular weight and molecular weight range, rate of excretion/elimination, and degree of branching, and the like. The present invention offers yet another property of dextran that can be modified and controlled to increase the usefulness of dextran, dextran formulations, and dextran conjugates.

Oxidation of the dextran molecule to produce dialdehyde-dextran, followed by a reduction step produces a modified dextran, an oxidized and reduced dextan, which diminishes or eliminates an allergic response to dextran. For example, as few as about 10% or as many as 100% of all, or of a class of, hydroxyl groups on a dextran can be oxidized and reduced to alter its biological properties. Preferably the hydroxyl groups are vicinal hydroxyl groups, and oxidation is accomplished employing periodate. Preferably, about 20% to about 80% of all, or of a class of, hydroxyl groups on a dextran can be oxidized and reduced to reduce the allergenicity of the modified dextran compared to the dextran before oxidation and reduction.

The present invention can be applied to native dextran, dextran that has already been modified by known methods or for known purposes (such as those described above), or to the dextran component of a conjugate. For example, an already formulated dextran product (such as Iron(III) Dextran for iron supplement, or Iron-Dextran for MRI enhancement) can be modified by oxidation and reduction to reduce or eliminate an allergenic response.

Although oxidation is the preferred method for modification of dextran to eliminate or reduce the allergenic response, other methods of chemical modification are also effective. For example, suitable modifications may include hydroxyethylation, alkylation, reduction, esterfication, and the like.

Method for Modifying Polysaccharide by Oxidation and Reduction

Modification of a polysaccharide, such as starch or dextran, can be carried out by dissolving the polysaccharide, such as starch or dextran, in an aqueous medium at a concentration of approximately 100 g/L. While stirring, a suitable oxidizing agent, preferably periodate, preferably a solution of $NaIO_4$, $NaIO_4$ solid, or $HIO_4$, is added to oxidize the polysaccharide, such as starch or dextran. The amount of oxidizing agent, such as $NaIO_4$, used will control the amount of oxidation or modification of the polysaccharide, such as starch or dextran. The reaction mixture is then purified by conventional methods to remove salts from the oxidation reaction and to recover the polysaccharide, such as starch or dextran, with dialdehyde and other aldehyde moieties formed by oxidation. Next, the polysaccharide, such as starch or dextran, with dialdehyde and other aldehyde moieties formed by oxidation are reduced. A preferred reducing agent is $NaBH_4$. The dialdehyde functional groups are thereby converted to dialcohol groups, and aldehydes are reduced as well. Finally the reaction mixture is again purified by conventional methods to remove salts from the reaction mixture.

Additional suitable methods for oxidizing and reducing polysaccharides, such as starch and dextran, are described in U.S. patent application Ser. No. 08/911,991, to be issued as U.S. Pat. No. 5,847,110 on Dec. 8, 1998, the disclosure of which is incorporated herein by reference.

The oxidized and reduced polysaccharide, such as oxidized and reduced starch or oxidized and reduced dextran, is then ready for formulation. Alternatively, prior to reduction of the oxidized polysaccharide, such as oxidized starch or oxidized dextran, the aldehyde functional groups on the oxidized polysaccharide, such as oxidized starch or oxidized dextran, can be conjugated to a drug, a chelator, or another active moiety to produce a conjugate.

The present method of oxidation and reduction has several advantages compared to other, previously available methods for modification of polysaccharides to alter their biological properties. Compared to, for example, hydroxyethylation, the degree of oxidation is much easier to control since the reaction with oxidizer is stoichiometric. Oxidation is more specific, typically being limited to only one site on a glucose, or other saccharide, sub-unit. In addition, reaction by-products of the oxidation reaction have low toxicity and are easily removed. Oxidation is cost effective since an oxidant such as periodic acid may be regenerated by an electrolytic process.

Conjugates Employing Oxidized and Reduced Polysaccharide

Covalently binding a chelator, or other molecule, to a polysaccharide has been discovered to be advantageous for several reasons. For example, binding to the polysaccharide can alter the distribution of the chelator, or other molecule, in the patient. For example, although not limiting to the present invention, it is believed that the conjugate of a chelator and polysaccharide is retained in the circulation to a greater degree than the chelator alone. Additional advantageous features of a conjugate can include altered biodistribution, diminished toxicity, increased stability of the chelator, or other molecule, in solution, formulations and plasma, and greater efficacy of the chelator, or other molecule.

The polysaccharide is preferably an oxidized and reduced polysaccharide. Polysaccharides suitable for oxidation and reduction include dextrans and hyaluronic acid, starch and starch derivatives, and the like. Polysaccharide starting materials such as dextrans and starches are commercially available as water-soluble preparations or as solutions. See *Remington's Pharmaceutical Sciences*, A. Osol., ed., Mack Publishing (16th ed. 1980) at pages 759–761. Polysaccharides of the invention include those described in U.S. Pat. Nos. 4,863,964, 5,217,998, and 5,268,165, the disclosures of which are incorporated herein by reference.

The oxidized and reduced polysaccharide is sufficiently stable to carry the chelator, or other molecule, in the patient for a sufficient time that it is effective for the desired biological or therapeutic purpose. In addition, the polysaccharide is sufficiently well-tolerated and non-toxic (e.g. nonallergenic) that the patient has no unacceptable adverse reactions to the treatment.

Preparing a Conjugate

There are several ways in which a chelator, or other molecule, can be covalently bonded to the polysaccharide or oxidized polysaccharide to form a conjugate. The chelator, or other molecule, is bound to the polysaccharide or oxidized polysaccharide in a manner such that its desired properties, as measured in vitro, remain substantial, and preferably on the order of the non-conjugated chelator, or other molecule. One preferred way to form conjugates of a chelator, or other molecule, with a polysaccharide or oxidized polysaccharide is to bind an amino group, such as a terminal amino group of deferoxamine, to the polysaccharide or oxidized polysaccharide. Such an amino group can form a covalent bond with a carboxyl group on a polysaccharide to form an amide linkage.

Preferably, an amino group of the chelator, or other molecule, will form a covalent bond with an aldehyde moiety. In an initial reaction, the amine on the chelator, or other molecule, reacts with the aldehyde to form a Schiff base, and the Schiff base is reduced in a second reaction to yield more stable covalent linkage. Aldehydic groups can be introduced into the polysaccharide by known techniques, e.g. by the oxidation of carbohydrates or other diols to dialdehydes with sodium metaperiodate. See, for example, M. B. Wilson, et al. in *Immunofluorescence and Related Staining Techniques*, W. Knapp et al., eds., Elsevier/North Holland Biomedical Press (1978) at page 215, Flernming et al., *Acta Biol. Med. Ger.*, 30, 177 (1973); and, S.-C. Tam et al., in *P.N.A.S. USA*, 73, 2128 (1976). In some applications, the terminal amino group on a chelator, or other molecule, can also be bonded to an amino group on the polymer directly, by the use of a dialdehyde linking agent such as glutaraldehyde, followed by reduction, e.g., with sodium borohydride.

More preferred chelator conjugates are prepared by covalently bonding deferoxamine to a pharmaceutically-acceptable polysaccharide or oxidized polysaccharide. Methods for the preparation of deferoxamine (N-[5-[3[(5-aminopentyl) hydroxycarbamoyl] propionamido] pentyl]-3-[[5-(Nhydroxyacetamido) pentyll carbamoyl] propionohydroxamic acid) and its pharmaceutically-acceptable salts have been disclosed, e.g., by Prelog et al., in *Helv. Chim. Acta.*, 45, 631 (1962); Bickel et al., *Helv. Chim. Acta*, 46 1385 (1963); in German Pat. Spec. 1,186,076 and in U.S. Pat. Nos. 4,419,365, 4,987,253, and 5,493,053, the disclosures of which are incorporated by reference herein. Such salts include the acid addition salts of methane sulfonic acid, phosphoric acid, acetic acid, lactic acid, tartaric acid, citric acid, and the like. Other suitable chelators include 2,3-dihydroxybenzoic acid, DTPA, rhodotorulic acid, cholylhydroxamic acid, ethylene diamine-N,N'-bis(2-hydroxyphenylacetic acid), isoniazid-pyridoxal hydrozone, 1,2-dimethyl-3-hydroxypyrid-4-one and nitrilotriacetate. These chelators can be used alone or in combination.

Methods for preparing chelator conjugates include the methods described in U.S. Pat. Nos. 4,863,964, 5,217,998, and 5,268,165, and in U.S. patent application Ser. No. 08/911,991, to be issued as U.S. Pat. No. 5,847,110 on Dec. 8, 1998, the disclosures of which are incorporated herein by reference.

The mole ratios of chelator or other molecule to polysaccharide attainable by reactions with carboxyl or carbonyl groups can vary widely, depending on factors such as the number of reactive groups on the polymer, steric hindrance, rate and extent of Schiff base or amide formation, and the like. More than one molecule of chelator or other molecule can be attached to each molecule of polysaccharide. As an example, about 0.7 g of deferoxamine can be bonded to about 2.5 g of reacted Dextran 40, via reaction of the deferoxamine with aldehyde groups introduced into the dextran, followed by reduction.

Administering the Oxidized and Reduced Polysaccharide

The oxidized and reduced polysaccharide can be delivered by a variety of routes effective to gain circulating and local levels sufficient to provide the desired biological or therapeutic effect. Typical routes of administration would be parenteral, such as intravenous or subcutaneous. The oxidized and reduced polysaccharide is preferably administered as a solution or suspension in an aqueous solvent that is compatible with administration to patients such as animals, mammals or humans. A preferred pharmaceutical composition is non-pyrogenic. Preferably oxidized and reduced polysaccharide is administered, as solutions, parenterally, such as by intramuscular, intraperitoneal, subcutaneous, intraocular, or intravenous injection or infusion, or via buccal, oral, pulmonary, rectal or vaginal routes. The appropriate dose will be adjusted in accord with appropriate clinical factors in the treating physician's judgment including: the disorder to be treated; the patient or patient's age, size and weight; the mode of administration; properties of the particular oxidized and reduced polysaccharide, and the like.

The present invention may be better understood with reference to the following examples. These examples are intended to be representative of specific embodiments of the invention, and are not intended as limiting the scope of the invention.

EXAMPLES

Example 1

Modification of Native Starch

The native starch employed was unmodified degraded waxy maize starch (MW 126,000), which was obtained from Laevosan (Linz, Austria) and is Lot 43572, PN 1021B. All water used for preparation of these modified polysaccharides was depyrogenated water, and all other vessels/utensils were depyrogenated prior to use. When possible, reactions and work-ups were performed in the laminar flow hood to preserve purity of these solutions, for intravenous and other parenteral administration. Reactions were performed at ambient room temperature and cooling was applied in some cases to prevent warming of the reaction mixture.

Experiment 1

Preparation of Modified Starch With 175 mM Periodate

In a clean, glass vessel 30 g of starch powder was dissolved in 300 mL of water. To this was slowly added 11.23 g of $NaIO_4$ (175 mM), and this mixture was stirred for 105 minutes. The resulting mixture was diafiltered (membrane: Pellicon 2 mini, 5K MWCO, 0.1 $m^2$) against water until the conductivity of the filtrate was 25 $\mu$S. The oxystarch concentration was then adjusted to 100 g/L. While stirring $NaBH_4$ (2.38 g) was added to the oxystarch solution (239 mL) to obtain a $NaBH_4$ concentration of 263 mM. The reaction was stirred for 2 hours. The resulting solution was diafiltered against water until the filtrate conductivity reaches 58 $\mu$S. The pH of the solution was then adjusted to 6.3 with HCl, and polymer concentration was adjusted to 102 g/L. Finally the chloride concentration was adjusted to 154 mM. The solution was then sterile filtered into glass vials, stoppered and stored at 4° C. This yielded approximately 192 mL of modified starch product in which approximately 28% of the glucose sub-units were modified.

Experiment 2

Preparation of Modified Starch With 222 mM Periodate

In a clean, glass vessel 30 g of starch powder was dissolved in 300 mL of water. To this was slowly added 14.25 g of $NaIO_4$ (222 mM), and the mixture was stirred for 60 minutes. The resulting mixture was diafiltered (membrane: Pellicon 2, 5K MWCO, 0.5 $m^2$) against water until the conductivity of the filtrate was 27 $\mu$S. The oxystarch concentration was then adjusted to 100 g/L. While stirring $NaBH_4$ (2.27 g) was added to the oxystarch solution (180 mL) to obtain a $NaBH_4$ concentration of 333 mM. The reaction was stirred for 190 minutes. The resulting solution was diafiltered against water until the filtrate conductivity reaches 35 $\mu$S. The pH of the solution was then adjusted to 6.5 with HCl, and polymer concentration was adjusted to 100 g/L. Finally the chloride concentration was adjusted to 154 mM. The solution was then sterile filtered into glass vials, stoppered and stored at 4° C. This yielded approximately 133 mL of modified starch product in which approximately 36% of the glucose sub-units were modified.

Experiment 3

Preparation of Modified Starch With 278 mM Periodate

In a clean, glass vessel 30 g of starch powder was dissolved in 300 mL of water. To this was slowly added 17.84 g of $NaIO_4$ (278 mM), and the mixture was stirred for 90 minutes. The resulting mixture was diafiltered (membrane: Pellicon 2, 5K MWCO, 0.5 $m^2$) against water until the conductivity of the filtrate was 13 $\mu$S. The oxystarch concentration was then adjusted to 100 g/L. While stirring $NaBH_4$ (3.09 g) was added to the oxystarch solution (196 mL) to obtain a $NaBH_4$ concentration of 417 mM. The reaction was stirred for 185 minutes. The resulting solution was diafiltered against water until the filtrate conductivity reaches 45 $\mu$S. The pH of the solution was then adjusted to 5.5 with HCl, and polymer concentration was adjusted to 100 g/L. Finally the chloride concentration was adjusted to 154 mM. The solution was then sterile filtered into glass vials, stoppered and stored at 4° C. This yielded approximately 151 mL of modified starch product in which approximately 45% of the glucose sub-units were modified.

Experiment 4

Preparation of Modified Starch With 334 mM Periodate

In a clean, glass vessel 30 g of starch powder was dissolved in 300 mL of water. To this was slowly added 21.43 g of NaIO$_4$ (334 mM), and the mixture was stirred for 105 minutes. The resulting mixture was diafiltered (membrane: Pellicon 2, 5K MWCO, 0.5 m$^2$) against water until the conductivity of the filtrate was 43 µS. The oxystarch concentration was then adjusted to 100 g/L. While stirring NaBH$_4$ (3.66 g) was added to the oxystarch solution (193 mL) to obtain a NaBH$_4$ concentration of 501 mM. The reaction was stirred for 185 minutes. The resulting solution was diafiltered against water until the filtrate conductivity reached 35 µS. The pH of the solution was then adjusted to 4.4 with HCl, and polymer concentration was adjusted to 100 g/L. Finally the chloride concentration was adjusted to 154 mM. The solution was then sterile filtered into glass vials, stoppered and stored at 4° C. This yielded approximately 127 mL of modified starch product in which approximately 54% of the glucose sub-units were modified.

Example 2—Oxidation and Reduction of Starch Slows Amylase Digestion

Modified starch products prepared above in Experiments 2, 3 and 4 of Example 1 were examined for rate of digestion by αamylase using gel permeation chromatography with refractive index and laser light scattering detection.

A solution of α-amylase (Sigma A-6255, Lot 33H8075, from porcine pancreas, Type 1-A DFP treated, 30 mg protein/mL, 790 units/mg protein) was prepared by diluting the stock solution 1:50 with 0.9% aqueous NaCi solution. The digestion samples were prepared in a glass test tube in the following manner: Into the tube were placed 0.5 mL of 0.9% aqueous NaCl, 0.1 mL of 50 mM CaCl$_2$, 0.1 mL HEPES (pH 7), and 10 µL of α-amylase solution (prepared above) and mixed well. Next was added 10.0 mL of modified (oxidized and reduced) starch (100 g/L) to the test tube, which was vortexed and allowed to stand at room temperature. At given time points 200 µL of amylase/starch solution was sampled, diluted with 0.88 mL of gel permeation chromatography (GPC) eluent and mixed well. This was then injected on a GPC column for measurement of the samples' molecular weight distribution.

FIG. 1 illustrates a plot of the change in the Weight Average Molecular Weight (WAMW) as a function of time for each of the modified starch products. These data are given in Table 1.

TABLE 1

Change in WAMW Over Time As a Percentage of Initial WAMW

| Time (hr) | 222 mM NaIO$_4$ (36% Modified) | 278 mM NaIO$_4$ (45% Modified) | 334 mM NaIO$_4$ (54% Modified) |
|---|---|---|---|
| 0.00 | 100% | 100% | 100% |
| 0.08 | 94% | 93% | 99% |
| 3.00 | 69% | 84% | 97% |
| 7.00 | 57% | 78% | 95% |
| 24.00 | 38% | 59% | 89% |

In each experiment, oxidation and reduction of starch slowed its degradation by amylase.

Example 3—Oxidized and Reduced Starch is Cleared More Slowly in Animals

In-vivo blood clearance in rats of several modified (oxidized and reduced) starches was examined. Modified starch products prepared above in Experiments 2 through 4 were administered i.v. (femoral vein) to Sprague-Dawley rats at a dosage of 10 mL/kg given as a bolus injection. Starch samples modified with 222 mM and 278 mM NaIO$_4$ were each injected into three animals. Two animals were injected with starch modified with 334 mM NaIO$_4$. Samples of blood were drawn from the femoral vein at 30 minutes, 1 hr, 2 hr, 4 hr and 8 hr. These samples were then assayed for modified starch concentration.

Figure 2:
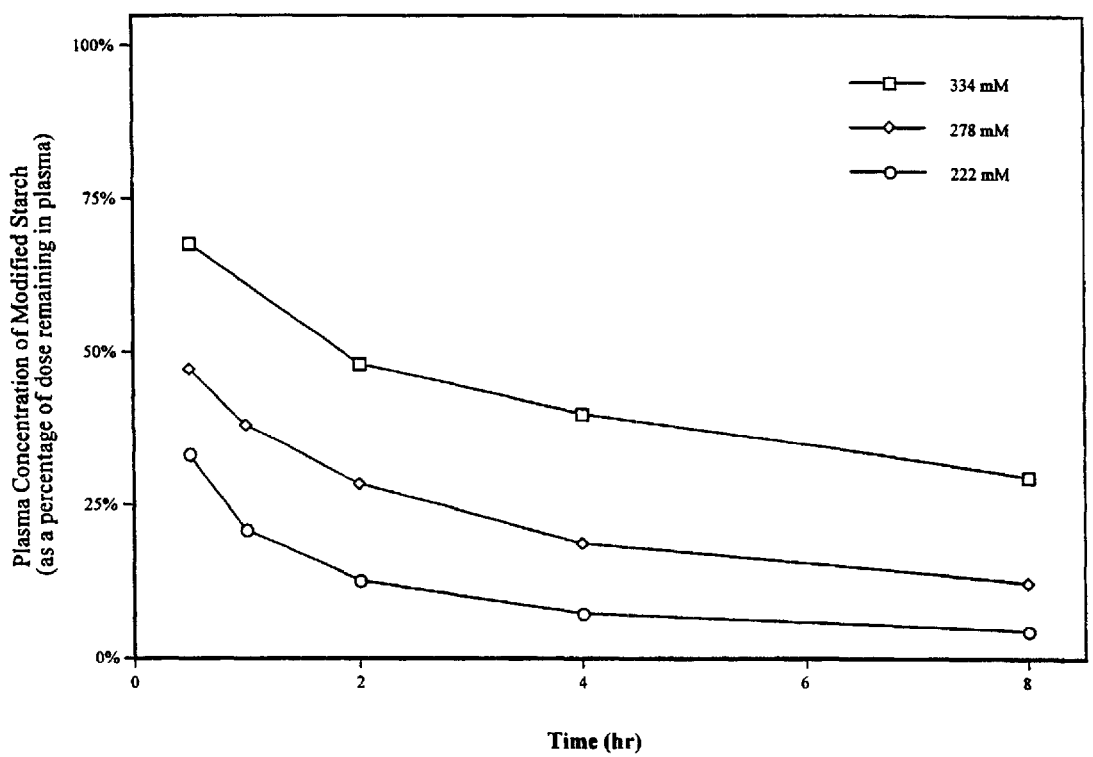
FIG. 2 shows a plot of the average blood levels of modified starch as a function of time.

FIG. 2 shows a plot of the average blood levels of modified starch as a function of time. These data are provided in Table 2.

TABLE 2

Average Blood Levels of Modified Starch Products (n = 3 animals) As a Percentage of Initial Dose Remaining in the Plasma

| Time (hr) | 222 mM NaIO$_4$ (36% Modified) | 278 mM NaIO$_4$ (45% Modified) | 334 mM NaIO$_4$ (54% Modified) |
|---|---|---|---|
| 0.5 | 33.1% | 47.0% | 67.7% |
| 1 | 20.3% | 37.9% | n/a |
| 2 | 12.6% | 28.4% | 48.1% |
| 4 | 7.4% | 18.6% | 39.7% |
| 8 | 4.3% | 12.3% | 29.6% |

In each experiment, oxidation and reduction of starch slowed its clearance from the animal.

Example 4—Modification of Starch in Synthesis of a Starch-Deferoxamine Conjugate The next several experiments detail preparation of DFO-starch products and oxidation and reduction of the starch or conjugate. Each used unmodified degraded waxy maize starch (starch) MW 126,000 or 46,000 and deferoxamine mesylate (DFO) as raw materials. The starch was obtained from Laevosan (Linz, Austria). The DFO was obtained from Pharmacia & Upjohn (Kalamazoo, Mich.) Lot 22ADF, PN 1001B. All water used for preparation of these batches is depyrogenated water, and all other vessels/utensils were depyrogenated prior to use. When possible, reactions and work-ups were performed in the laminar flow hood to preserve purity of these solutions. All reactions were performed at or slightly below ambient room (laboratory) temperature.

Experiment 1

Preparation of DFO-Starch Conjugate With 34 mM Chelator and 150 mM Periodate

In a clean, glass vessel 99.8 g of starch powder (MW 46,000) was dissolved in 1000 mL of water. Next, 32.0 g of NaIO$_4$ (150 mM) was added to the mixture, and stirred for 90 minutes. The resulting mixture was diafiltered (membrane: Biomax 5K MWCO) against water until the conductivity of the filtrate was 103 µS. The oxystarch concentration was then adjusted to 245 g/L. The reaction volume was adjusted to 288 mL with water and ethanol to provide a mixture that was 30% ethanol by volume. DFO (22.26 g) was added while stirring. Stirring was continued for 1 hour, after which 5.65 mL of 8M borane pyridine complex (BPC) was added to the reaction mixture. The mixture was then stirred for 20 hours. At the end of this reaction period, an additional 144 mL of water was added to the mixture followed by slow addition of 3.87 g NaBH$_4$ (225 mM). Stirring was continued for 1 hour, after which the reaction mixture was diafiltered against water until the filtrate conductivity was 30 µS. The pH was then adjusted to 6.0 with HCl, the chloride concentration was adjusted to provide a final concentration of 154 mM, and the polymer concentration was adjusted to 100 g/L. Finally, the solution was sterile filtered into glass vials, stoppered and stored at 4° C. This yielded approximately 515 mL of starch-DFO product in which approximately 24% of the glucose sub-units were modified, and had a high molecular weight chelator concentration of 34 mM at a starch-DFO concentration of 100 g/l.

Experiment 2

Preparation of DFO-Starch Conjugate With 45 mM Chelator and 550 mM Periodate

In a clean, glass vessel 100 g of starch powder (MW 46,000) was dissolved in 970 mL of water. Next, 117.7 g of $NaIO_4$ (550 mM) was added to the mixture, and stirred for 60 minutes. The resulting mixture was diafiltered (membrane: Pellicon 2 Biomax 5K MWCO) against water until the conductivity of the filtrate was 167 $\mu$S. The oxystarch concentration was then adjusted to 166 g/L. The reaction volume was adjusted to 540 mL with water and ethanol to provide a mixture that was 30% ethanol by volume. DFO (27.09 g) was added while stirring. Stirring was continued for 1 hour, after which 13.8 mL of 8M borane pyridine complex (BPC) was added to the reaction mixture. The mixture was then stirred for 18 hours, after which 7 mL of BPC was added and stirring continued for another 2 hours. At the end of this reaction period, an additional 572 mL of water was added to the mixture followed by slow addition of 17.17 g $NaBH_4$ (825 mM). Stirring was continued for 3 hours, after which the reaction mixture was diafiltered against water until the filtrate conductivity was 124 $\mu$S. The pH was then adjusted to 6.0 with HCl, the chloride concentration was adjusted to provide a final concentration of 154 mM, and the polymer concentration was adjusted to 100 g/L. Finally, the solution was sterile filtered into glass vials, stoppered and stored at 4° C. This yielded approximately 515 mL of starch-DFO product in which approximately 89% of the glucose sub-units were modified, and had a high molecular weight chelator concentration of 45 mM at a starch-DFO concentration of 100 g/l.

Experiment 3

Preparation of DFO-Starch Conjugate With 36 mM Chelator and 150 mM Periodate

In a clean, glass vessel 50 g of starch powder (MW 126,000) was dissolved in 465 mL of water. Next 16.0 g of $NaIO_4$ (150 mM) was added to the mixture, and stirred for 60 minutes. The resulting mixture was diafiltered (membrane: Pellicon 2 mini, 5K MWCO) against water until the conductivity of the filtrate was 136 $\mu$S. The oxystarch concentration was then adjusted to 165 g/L. The reaction volume was adjusted to 385 mL with water and ethanol to provide a mixture that was 30% ethanol by volume. DFO (19.51 g) was added while stirring. Stirring was continued for 5 minutes, after which 4.95 mL of 8M borane pyridine complex (BPC) was added to the reaction mixture. The mixture was then stirred for 19 hours. At the end of this reaction period 3.39 g $NaBH_4$ (225 mM) was slowly added to the reaction vessel while stirring. Stirring was continued for 90 minutes, after which the reaction mixture was diafiltered against water until the filtrate conductivity was 97 $\mu$S. The pH was then adjusted to 6.0 with HCl, the chloride concentration was adjusted to provide a final concentration of 154 mM, and the polymer concentration was adjusted to 100 g/L. Finally, the solution was sterile filtered into glass vials, stoppered and stored at 4° C. This yielded approximately 470 mL of starch-DFO product in which approximately 24% of the glucose sub-units were modified, and had a high molecular weight chelator concentration of 36 mM at a starch-DFO concentration of 100 g/l.

Experiment 4

Preparation of DFO-Starch Conjugate With 47 mM Chelator and 550 mM Periodate

In a clean, glass vessel 50 g of starch powder (MW 126,000) was dissolved in water to a final volume of 500 mL. Next 58.8 g of $NaIO_4$ (550 mM) was added to the mixture, and stirred for 60 minutes. The resulting mixture was diafiltered (membrane: Pellicon 2 mini, 5K MWCO) against water until the conductivity of the filtrate was 167 $\mu$S. The oxystarch concentration was then adjusted to 160 g/L. The reaction volume was adjusted to 395 mL with water and ethanol to provide a mixture that was 30% ethanol by volume. DFO (19.28 g) was added while stirring. Stirring was continued for 60 minutes, after which 14.7 mL of 8M borane pyridine complex (BPC) was added to the reaction mixture. The mixture was then stirred for 20 hours. At the end of this reaction period 12.2 g $NaBH_4$ (825 mM) was slowly added to the reaction vessel while stirring. Stirring was continued for 180 minutes, after which the reaction mixture was diafiltered against water until the filtrate conductivity was 144 $\mu$S. The pH was then adjusted to 6.0 with HCl, the chloride concentration was adjusted to provide a final concentration of 154 mM, and the polymer concentration was adjusted to 100 g/L. Finally, the solution was sterile filtered into glass vials, stoppered and stored at 4° C. This yielded approximately 517 mL of starch-DFO product in which approximately 89% of the glucose sub-units were modified, and has a high molecular weight chelator concentration of 47 mM at a starch-DFO concentration of 100 g/l.

Experiment 5

Preparation of DFO-Starch Conjugate With 40 mM Chelator and 222 mM Periodate

In a clean, glass vessel 50 g of starch powder (MW 126,000) was dissolved in 473 mL of water. Next 23.74 g of $NaIO_4$ (222 mM) was added to the mixture, and stirred for 65 minutes. The resulting mixture was diafiltered (membrane: Biomax Pellicon 2 mini, 5K MWCO) against water until the conductivity of the filtrate was 90 $\mu$S. The oxystarch concentration was then adjusted to 163 g/L. The reaction volume was adjusted to 388 mL with water and ethanol to provide a mixture that was 30% ethanol by volume. DFO (19.47 g) was added while stirring. Stirring was continued for 15 minutes, after which 7.42 mL of 8M borane pyridine complex (BPC) was added to the reaction mixture. The mixture was then stirred for 20 hours. At the end of this reaction period 4.99 g $NaBH_4$ (333 mM) was slowly added to the reaction vessel while stirring. Stirring was continued for 200 minutes, after which the reaction mixture was diafiltered against water until the filtrate conductivity was 96 $\mu$S. The pH was then adjusted to 6.0 with HCl, the chloride concentration was adjusted to provide a final concentration of 154 mM, and the polymer concentration was adjusted to 100 g/L. Finally, the solution was sterile filtered into glass vials, stoppered and stored at 4° C. This yielded approximately 529 mL of starch-DFO product in which approximately 36% of the glucose sub-units were modified, and had a high molecular weight chelator concentration of 40 mM at a starch-DFO concentration of 100 g/l.

Experiment 6

Preparation of DFO-Starch Conjugate With 42 mM chelator and 278 mM Periodate

In a clean, glass vessel 50 g of starch powder (MW 126,000) was dissolved in 445 mL of water. Next 29.71 g of NaIO$_4$ (278 mM) was added to the mixture, and stirred for 65 minutes. The resulting mixture was diafiltered (membrane: Biomax Pellicon 2 mini, 5K MWCO) against water until the conductivity of the filtrate was 107 µS. The oxystarch concentration was then adjusted to 169 g/L. The reaction volume was adjusted to 393 mL with water and ethanol to provide a mixture that was 30% ethanol by volume. DFO (19.72 g) was added while stirring. Stirring was continued for 18 minutes, after which 10.00 mL of 8M borane pyridine complex (BPC) was added to the reaction mixture. The mixture was then stirred for 20 hours. At the end of this reaction period 6.39 g NaBH$_4$ (417 mM) was slowly added to the reaction vessel while stirring. Stirring was continued for 180 minutes, after which the reaction mixture was diafiltered against water until the filtrate conductivity was 91 µS. The pH was then adjusted to 6.0 with HCl, the chloride concentration was adjusted to provide a final concentration of 154 mM, and the polymer concentration was adjusted to 100 g/L. Finally, the solution was sterile filtered into glass vials, stoppered and stored at 4° C. This yielded approximately 558 mL of starch-DFO product in which approximately 45% of the glucose sub-units were modified, and had a high molecular weight chelator concentration of 42 mM at a starch-DFO concentration of 100 g/l.

Experiment 7

Preparation of DFO-Starch Conjugate With 43 mM Chelator and 334 mM Periodate

In a clean, glass vessel 50 g of starch powder (MW 126,000) was dissolved in 450 mL of water. Next 35.72 g of NaIO$_4$ (334 mM) was added to the mixture, and stirred for 60 minutes. The resulting mixture was diafiltered (membrane: Biomax Pellicon 2 mini, 5K MWCO) against water until the conductivity of the filtrate was 110 µS. The oxystarch concentration was then adjusted to 181 g/L. The reaction volume was adjusted to 335 mL with water and ethanol to provide a mixture that was 30% ethanol by volume. DFO (16.98 g) was added while stirring. Stirring was continued for 15 minutes, after which 10.80 mL of 8M borane pyridine complex (BPC) was added to the reaction mixture. The mixture was then stirred for 20 hours. At the end of this reaction period 6.54 g NaBH$_4$ (501 mM) was slowly added to the reaction vessel while stirring. Stirring was continued for 170 minutes, after which the reaction mixture was diafiltered against water until the filtrate conductivity was 108 µS. The pH was then adjusted to 6.0 with HCl, the chloride concentration was adjusted to provide a final concentration of 154 mM, and the polymer concentration was adjusted to 100 g/L. Finally, the solution was sterile filtered into glass vials, stoppered and stored at 4° C. This yielded approximately 474 mL of starch-DFO product in which approximately 54% of the glucose sub-units were modified, and had a high molecular weight chelator concentration of 43 mM at a starch-DFO concentration of 100 g/l.

Example 5—Oxidation and Reduction of Starch Slows Amylase Digestion of DFO-Starch Conjugates DFO-starch conjugates prepared above in Experiments 3 and 4 of Examined 4 were examined for rate of digestion by α-amnylase using gel permeation chromatography with refractive index and laser light scattering detection.

The congestion samples were prepared in a manner similar to the procedure outline in example 2. The digested samples were injected on the GPC column for measurement of the sample molecular weight distribution.

Figure 3:
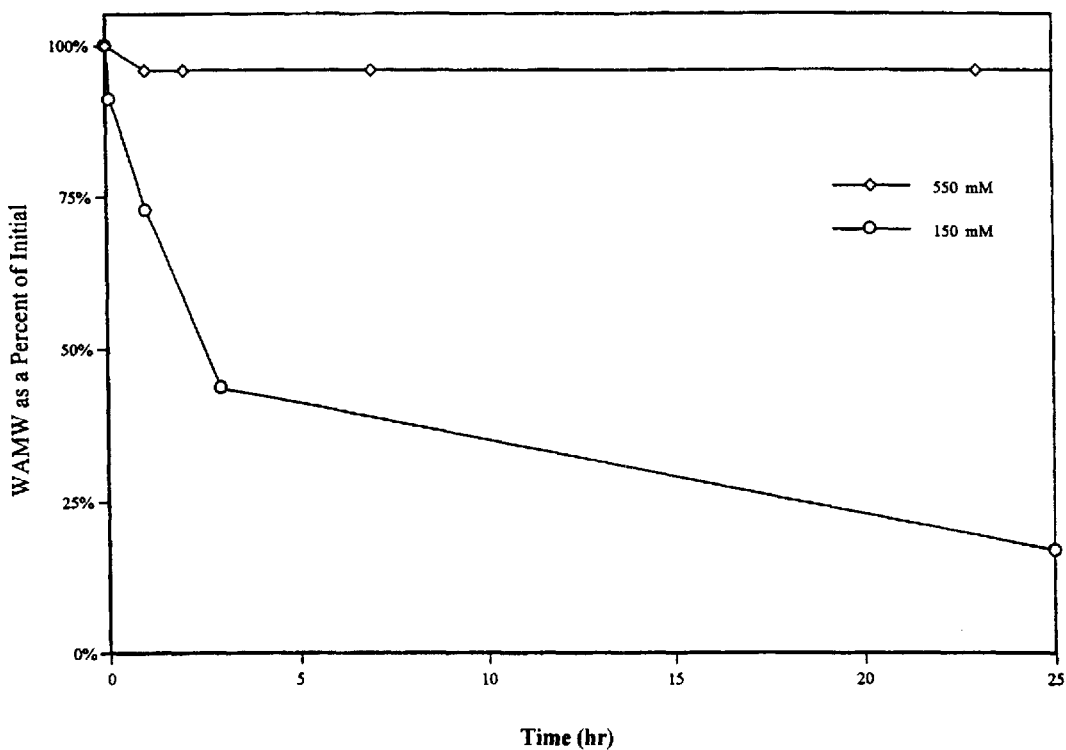
FIG. 3 provides a plot of the change in the WAMW as a function of time for each of the oxidized and reduced starch-DFO conjugates upon treatment with amylase.

FIG. 3 provides a plot of the change in the Weight Average Molecular Weight (WAMW) as a function of time for each of the modified starch products. These data are given in Table 3.

TABLE 3

Decrease in Weight Average Molecular Weight Upon Incubation with Amylase Expressed as a Percentage of Initial WAMW

| Time (hr) | 150 mM NaIO$_4$ (~24% Modified) | 550 mM NaIO$_4$ (~89% Modified) |
|---|---|---|
| 0.00 | 100.0% | 100.0% |
| 0.08 | 91.0% | n/a |
| 1 | 72.7% | 95.6% |
| 2 | n/a | 95.6% |
| 3 | 43.7% | n/a |
| 7 | n/a | 95.6% |
| 23 | n/a | 95.6% |
| 25 | 17.0% | n/a |
| 168 | n/a | 95.6% | n/a - not available

In each experiment, an increased extent of oxidation and reduction of starch slowed the rate of degradation by amylase of the starch-DFO conjugate.

Example 6—Increasing the Oxidation and Reduction of a Starch-DFO Conjugate Slows Clearance in Animals In-vivo blood clearance in rats of several DFO-oxidized and reduced starch conjugates was examined. Several DFO-oxidized and reduced starch conjugates as prepared above in Experiments 1 through 7 of Example 4 were administered i.v. (femoral vein) to Sprague-Dawley rats at a dosage of 10 mL/kg given as a 30 minute infusion. In all cases either two or three animals were used for this experiment. Samples of blood were drawn from the femoral vein at various time points. These samples were then assayed for DFO-Starch conjugate concentration.

Figure 4:
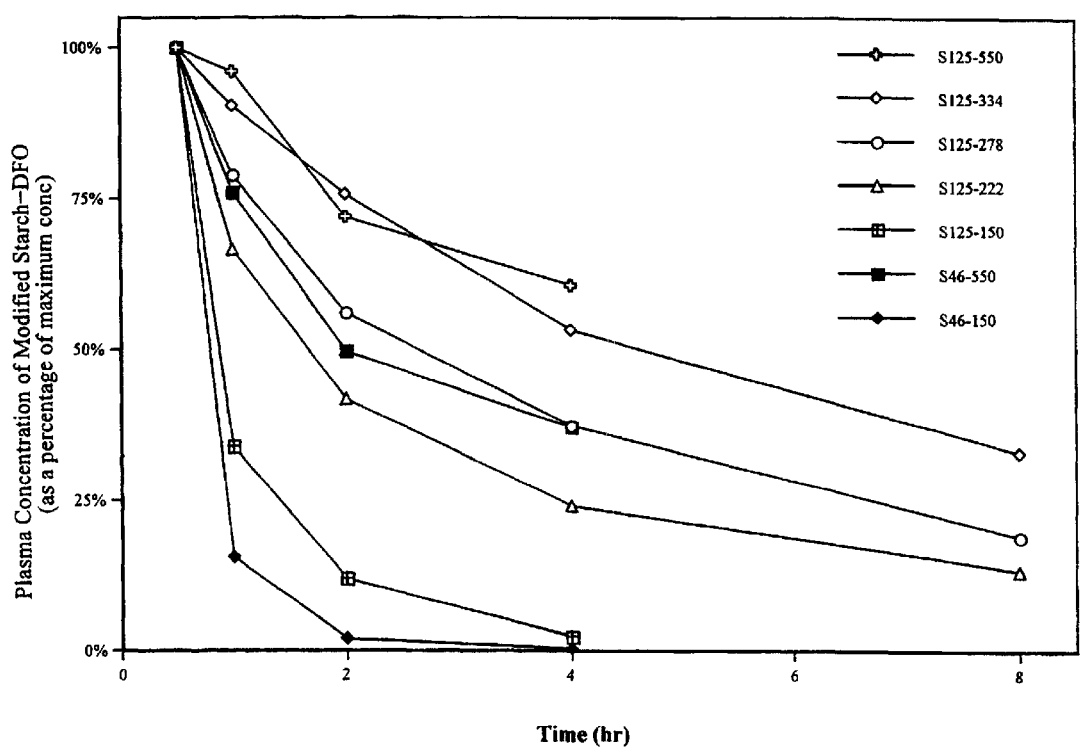
FIG. 4 shows a plot of the average blood levels of oxidized and reduced starch-DFO conjugates as a function of time.

FIG. 4 shows a plot of the average blood levels of DFO-Starch conjugate as a function of time. Experiments 1 and 2 employed starch having a molecular weight of 46,000. Experiments 3–7 employed starch having a molecular weight of 126,000. These data are provided in Table 4.

TABLE 4

Average Blood Clearance of DFO-Starch Conjugate Products As a Percentage of Plasma Concentration at 30 min.

| Time (hr) | Exp. 1 24% Mod | Exp. 2 89% Mod | Exp. 3 24% Mod | Exp. 4 89% Mod | Exp. 5 36% Mod | Exp. 6 45% Mod | Exp. 7 54% Mod |
|---|---|---|---|---|---|---|---|
| 0.5 | 100.0% | 100.0% | 100.0% | 100.0% | 100.0% | 100.0% | 100.0% |
| 1 | 15.3% | 76.0% | 33.7% | 96.0% | 66.4% | 78.8% | 90.1% |
| 2 | 2.0% | 49.7% | 11.9% | 71.9% | 41.6% | 55.9% | 75.6% |
| 4 | 0.6% | 36.9% | 2.3% | 60.5% | 23.8% | 37.2% | 53.2% |
| 8 | n/a | n/a | n/a | n/a | 13.0% | 18.7% | 32.8% | n/a—not available

An increased extent of oxidation and reduction of the starch slowed clearance of the starch -DFO conjugate from the animal.

Example 7—Modification of Dextran

Dextran modification was carried out by a slight modification of the method described in Example 1 for oxidizing starch. Briefly, dextran was dissolved in an aqueous medium at a concentration of approximately 100 g/L and while stirring, then was added a solution of $NaIO_4$ (or $NaIO_4$ in solid form) to oxidize the dextran. The amount of $NaIO_4$ used controlled the amount of dextran oxidation. The reaction mixture was then purified to remove salts from the oxidation reaction. Next, the resultant dialdehyde groups (formed by the oxidation reaction) were reduced to alcohol groups using $NaBH_4$. Finally the reaction mixture was again purified to remove salts from the reaction mixture. The "modified dextran" was then ready for formulation or further modification.

Example 8—Reduced Allergenicity of Oxidized and Reduced Dextran

Oxidized and reduced dextran was administered i.v. to Sprague Dawley Dawley rats at a dosage of 40 mL/kg over 30 minutes. About 100% of the vicinal hydroxyls on the dextran had been oxidized with periodate and reduced. A very minor allergic reaction was observed as demonstrated by slight inflation of the front paw pads (but not rear paw pads). After dosing the animal fully recovered from anesthesia In contrast, when an equivalent dose of native dextran was infused into a rat a very severe allergic reaction was observed after 15 minutes, approximately half way through the dose, the paw pads (front and rear) swelled, and the dosing was halted. Soon after termination of dosing the animal's tail and body became severely edematous, and the animal died at this point. It is believed that the death was caused by suffocation due to constriction of the air passageway brought on by an allergic reaction to the dextran. This strain of rat is known to be allergic to dextran.

The invention has been described with reference to various specific and preferred embodiments and techniques. However, it should be understood that many variations and modifications may be made while remaining within the spirit and scope of the invention. All publications and patent applications in this specification are indicative of the level of ordinary skill in the art to which this invention pertains.

What is claimed is:

1. A pharmaceutical composition comprising a partially oxidized and reduced water-soluble polysaccharide, wherein the polysaccharide is unmodified starch and a pharmaceutically acceptable vehicle, wherein about 20% to 80% of vicinal hydroxyl groups of the polysaccharide have been oxidized.

2. The pharmaceutical composition of claim 1, wherein the extent of oxidation and reduction of the soluble starch is effective to provide a longer vascular half-life than native starch.

3. The pharmaceutical composition of claim 1, wherein the oxidized and reduced soluble starch is a component of a Schiff base conjugate of the oxidized and reduced soluble starch.

4. The pharmaceutical composition of claim 3, wherein the conjugate of the oxidized and reduced soluble starch is a chelator.

5. The pharmaceutical composition of claim 4, wherein the chelator is deferoxamine.

6. The pharmaceutical composition of claim 1, wherein about 30% to about 60% of vicinal hydroxyl groups of the polysaccharide have been oxidized.

7. A method of increasing the vascular half life of starch comprising oxidizing about 20% to about 90% of vicinal hydroxyl groups of the unmodified starch, reducing the oxidized starch, and administering the oxidized and reduced starch into the circulation of a mammal.

8. The method of claim 7, comprising oxidizing about 30% to about 60% of vicinal hydroxyl groups of the starch.

9. The method of claim 7, further comprising forming a Schiff base conjugate of the starch.

10. The method of claim 9, wherein forming the conjugate comprises reacting the starch with a chelator.

11. The method of claim 10, wherein the chelator is deferoxamine.

* * * * *